(12) United States Patent
Hall

(10) Patent No.: US 6,796,944 B2
(45) Date of Patent: Sep. 28, 2004

(54) DISPLAY FOR SUBTRACTION IMAGING TECHNIQUES

(75) Inventor: Anne Hall, New Berlin, WI (US)

(73) Assignee: GE Medical Systems Global Technology, LLC, Waukesha, WI (US)

(*) Notice: Subject to any disclaimer, the term of this patent is extended or adjusted under 35 U.S.C. 154(b) by 305 days.

(21) Appl. No.: 10/063,847

(22) Filed: May 17, 2002

(65) Prior Publication Data

US 2003/0216644 A1 Nov. 20, 2003

(51) Int. Cl.⁷ .................................................. A61B 8/00
(52) U.S. Cl. ...................................... 600/443; 600/454
(58) Field of Search ............................... 600/437–472; 73/625, 626; 128/916; 367/7, 11, 130, 138

(56) References Cited

U.S. PATENT DOCUMENTS

| | | | | |
|---|---|---|---|---|
| 5,456,257 A | * | 10/1995 | Johnson et al. | 600/458 |
| 5,706,819 A | * | 1/1998 | Hwang et al. | 600/458 |
| 5,724,976 A | * | 3/1998 | Mine et al. | 600/459 |
| 5,860,931 A | * | 1/1999 | Chandler | 600/458 |
| 5,961,464 A | * | 10/1999 | Poland | 600/458 |
| 5,980,459 A | | 11/1999 | Chiao et al. | 600/447 |
| 6,074,348 A | | 6/2000 | Chiao et al. | 600/443 |
| 6,108,572 A | | 8/2000 | Panda et al. | 600/407 |
| 6,210,332 B1 | | 4/2001 | Chiao et al. | 600/443 |
| 6,312,384 B1 | | 11/2001 | Chiao | 600/443 |
| 6,340,348 B1 | | 1/2002 | Krishnan et al. | 600/447 |
| 2001/0044278 A1 | | 11/2001 | Chiao et al. | 445/67.1 |

* cited by examiner

*Primary Examiner*—Ali Imam
(74) *Attorney, Agent, or Firm*—Cantor Colburn LLP (57) ABSTRACT

A method and apparatus for displaying reference background and flow ultrasound images. The method comprises: transmitting at least first and second broadband pulses to a common transmit focal position; receiving at least first and second ultrasound reflections associated with the at least first and second broadband pulses; forming a flow/contrast agent signal component based on the at least first and second ultrasound reflections; forming a B-mode background signal component based on independent processing of at least one of the at least first and second ultrasound reflections; and displaying an ultrasound image including a flow image component in a first image portion of a display and a B-mode reference image component based on at least one of the at least first and second ultrasound reflections, said B-mode reference image component displayed in a second image portion of said display.

40 Claims, 6 Drawing Sheets

DISPLAY FOR SUBTRACTION IMAGING TECHNIQUES

BACKGROUND OF THE INVENTION

Conventional ultrasound scanners create two-dimensional B-mode images of tissue in which the brightness of a pixel is based on the intensity of the echo return. In a so-called "color flow" mode, the flow of blood or movement of tissue can be imaged. Conventional ultrasound flow imaging methods typically use either the Doppler principle or a time-domain cross-correlation method to estimate the average flow velocity, which is then displayed in color overlaid on a B-mode image.

Measurement of blood flow in the heart and vessels using the Doppler effect is well known. The frequency shift of backscattered ultrasound waves may be used to measure the velocity of the back-scatterers from tissue or blood. The frequency of the backscattered signal increases when blood flows toward the transducer and decreases when blood flows away from the transducer, the amount of increase or decrease being proportional to the velocity of the blood flow. Thus this frequency shift may be used to estimate the average flow velocity, which is displayed using different colors to represent speed and direction of flow. The color flow velocity mode displays hundreds of adjacent sample volumes simultaneously, all color-coded to represent each sample volume's velocity.

The resulting flow image may be combined with a stationary tissue (i.e., B-mode) image acquired by detecting either the fundamental or (sub)harmonic signal components, either by summation or as an overlay in order to provide anatomical landmarks. An advantage of the overlay is that it may be done in color so that the flow regions stand out clearly. However, this method requires a more complex display. Furthermore, the flash artifacts resulting from surrounding tissue motion are severe. Injection of the background B-mode image by summation (either coherent or incoherent) results in more benign flash artifacts. In either case, however, additional firings beyond those used for flow imaging are required to acquire the imaging data representing stationary tissue.

An alternative method for imaging blood flow is B-flow. In B-flow, high spatial resolution is achieved by using broadband pulses, while high frame rate is achieved by using small packet sizes. High SNR/dynamic range is maintained by using coded excitation. Flow sensitivity in the range direction is highest and arises from pulse-to-pulse RF decorrelation, while flow sensitivity in the cross-range direction is due to pulse-to-pulse amplitude decorrelation as a group of reflectors (e.g. blood or contrast agents) flows across the beam profile.

The method includes transmitting a small packet of coded broadband pulses with a given pulse repetition interval to a transmit focal position. The packet size is made small (e.g., 2–4 firings) to achieve high frame rate, with the undesirable side effect of reduced SNR. SNR can be optionally recovered using coded excitation. A coded sequence of broadband pulses (centered at a fundamental frequency) is transmitted multiple times to a particular transmit focal position, each coded sequence constituting one firing. On receive, the receive pulses acquired for each firing are decoded and bandpass filtered, e.g., to isolate a spatially compressed pulse centered at the fundamental frequency. The backscattered signals from this sequence of firings are then filtered in slow time to remove echoes from stationary or slowly moving reflectors along the transmit path. The slow-time filtering is preferably performed by a high-pass FIR (finite impulse response) or IIR (infinite impulse response) wall filter, which increases the flow signal-to-clutter ratio. A flow image is formed by scanning the transmit focal position across the region of interest. Frame rate may be increased by simultaneously processing more than one receive vector from a single transmit vector with parallel receive hardware. The packet size, pulse repetition interval (PRI) and region of interest (ROI) may be optionally controlled by the user.

When imaging blood flow of very small blood vessels often down to the perfusion bed of the organ, the signals are of such low amplitude and the blood moving so slowly that conventional flow imaging techniques are not able to extract an adequate flow signal. In cases like this, contrast agents such as gas-filled microbubbles are optionally injected into the blood to serve as markers for imaging blood flow. As previously described above, a coded sequence of broadband pulses is transmitted multiple times to a particular transmit focal position. Fundamental and (sub/ultra) harmonic signals are generated from interaction between the transmitted ultrasound pulses and the propagation medium, especially the injected contrast agents. On receive, the receive signals are decoded and bandpass filtered to selectively isolate the fundamental or (sub/ultra) harmonic signals. These isolated selectively filtered signals are then high-pass filtered across firings using a conventional wall filter. As a result of this filtering, selectively filtered signals reflected from non-stationary tissue or flow regions along the transmit path are extracted, while received energy at the frequencies which would have contributed to undesirable stationary tissue signal is suppressed.

The imaging modes described above reduce the signal from normal surrounding tissue to allow the user to effectively image signals substantially lower in amplitude. In the case of Coded Harmonic Angio (CHA) and Coded Angio (CA) modes, both developed for contrast agent imaging, the signal is that from injected contrast agents in very small blood vessels often down to the perfusion bed of an organ. In the case of B-flow mode, the user is able to image blood flow using (unlike Doppler) the high frequency, wideband imaging pulses commonly used for B-mode imaging, with frame rates that are comparable to B-mode.

Unfortunately, the absence of the surrounding tissue background that enables good visualization of these low lying signals makes it very difficult for the user to do active imaging, since the visualization of the anatomical landmarks allowing the user to optimally position the probe is limited. For certain applications, such as the early detection of certain vascular diseases, the limited tissue background imaging associated with the blood flow imaging is not ideal. More specifically, if the resolution of the background imaging was clear, the background image would provide a reference image that can be used by a sonographer to establish a reference for the anatomy being scanned. Unfortunately, using the present non-Doppler based methods of blood flow imaging described above often results in little or no background tissue imaging. Therefore, it would be desirable to provide the user a background tissue image, without sacrificing the system frame rate or destroying the imaging resolution of the blood flow low amplitude signals.

BRIEF DESCRIPTION OF THE INVENTION

The above discussed and other drawbacks and deficiencies are overcome or alleviated by a method for displaying flow and reference background ultrasound images. The method comprises: transmitting at least first and second broadband pulses to a common transmit focal position; receiving at least first and second ultrasound reflections associated with the at least first and second broadband pulses; forming a flow and/or contrast agent signal component based on the at least first and second ultrasound reflections; forming a B-mode background signal component based on independent processing of at least one of the at least first and second ultrasound reflections; and displaying an ultrasound image including a flow/contrast agent image component in a first image portion of a display and a B-mode reference image component based on at least one of the at least first and second ultrasound reflections, said B-mode reference image component displayed in a second image portion of said display.

In an alternative embodiment, an ultrasound medical diagnostic system for imaging stationary and moving reflectors for an area of interest in a patient is disclosed. The ultrasound diagnostic system includes a transmitter for transmitting a sequence of at least two pulses to a transmit focal position and a receiver for receiving at least two echo signals associated with the sequence of at least two pulses. The echo signals contain a fundamental frequency component. The system further includes a first display processor configured to receive and process the at least two echo signals and is configured having a filter for supplying a filtered signal containing flow/contrast agent image information for moving reflectors based on the at least two echo signals. Also included is a second display processor configured to receive and independently process at least one of the at least two echo signals containing B-mode information for stationary reflectors based on the at least two echo signals, the B-mode information for stationary reflectors including said fundamental frequency component. A display is included for displaying a flow/contrast agent image of moving reflectors based on the filtered signal and a B-mode reference image of stationary reflectors based on the at least one of at least two echo signals supplied by the second display processor.

The above discussed and other features and advantages of the present invention will be appreciated and understood by those skilled in the art from the following detailed description and drawings.

BRIEF DESCRIPTION OF THE DRAWINGS

Referring to the exemplary drawings wherein like elements are numbered alike in the several Figures.

DETAILED DESCRIPTION OF THE INVENTION

Figure 1:
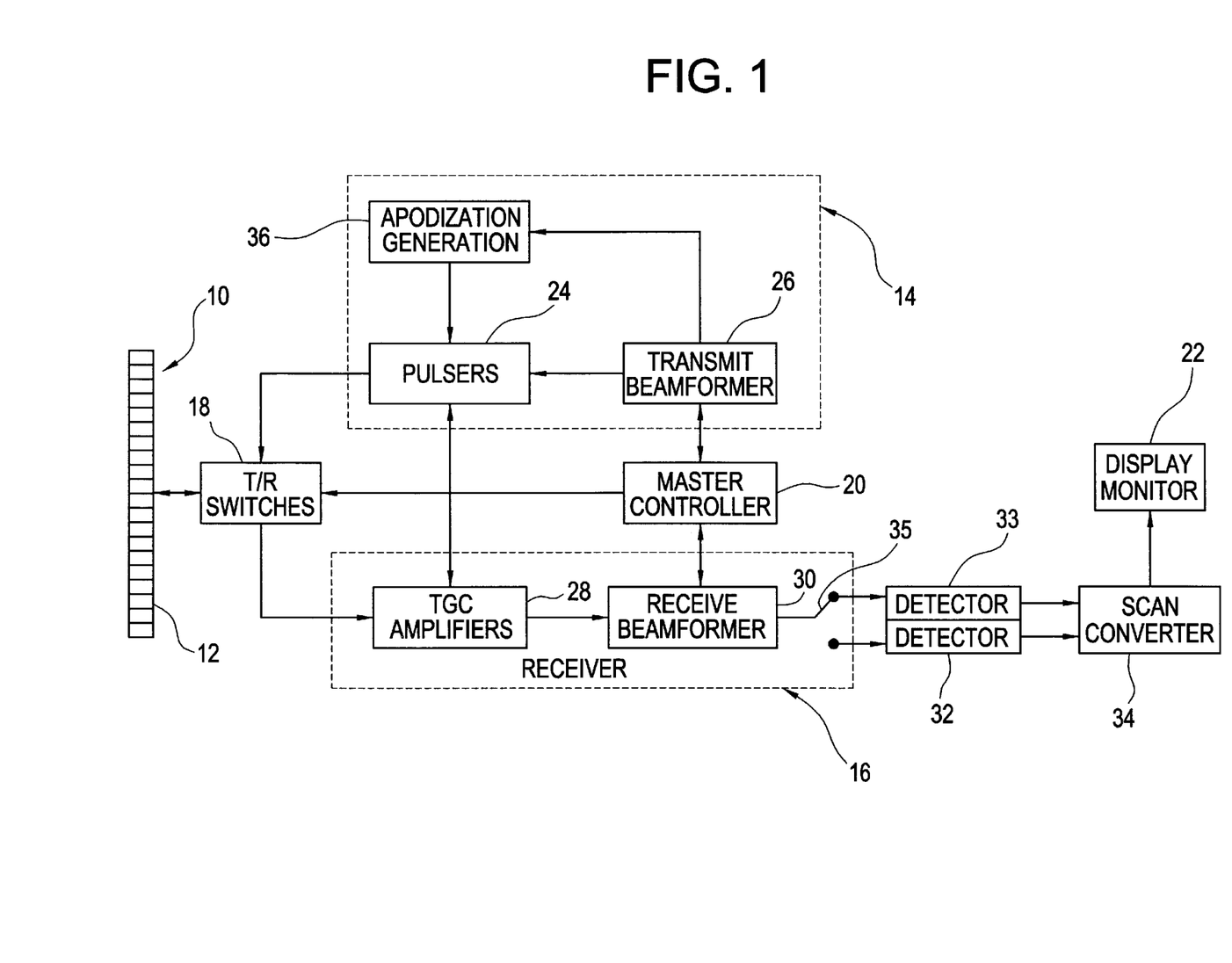
FIG. 1 is a block diagram of a conventional B-mode ultrasound imaging system switchable between a B-mode processor and a second colorflow processor for processing corresponding transmit firings.

A conventional ultrasonic imaging system is depicted in FIG. 1. The system comprises a transducer array 10 comprising a plurality of separately driven transducer elements 12, each of which produces a burst of ultrasonic energy when energized by a pulsed waveform produced by a transmitter 14. The ultrasonic energy reflected back to transducer array 10 from the object under study is converted to an electrical signal by each receiving transducer element 12 and applied separately to a receiver 16 through a set of transmit/receive (T/R) switches 18. The T/R switches 18 are typically diodes which protect the receive electronics from the high voltages generated by the transmit electronics. The transmit signal causes the diodes to shut off or limit the signal to the receiver. Transmitter 14 and receiver 16 are operated under control of a master controller 20 responsive to commands by a human operator. A complete scan is performed by acquiring a series of echoes in which transmitter 14 is gated ON momentarily to energize each transducer element 12, and the subsequent echo signals produced by each transducer element 12 are applied to receiver 16. A channel may begin reception while another channel is still transmitting. Receiver 16 combines the separate echo signals from each transducer element to produce a single echo signal which is used to produce a line in an image on a display monitor 22.

Under the direction of master controller 20, transmitter 14 drives transducer array 10 such that the ultrasonic energy is transmitted as a directed focused beam. To accomplish this, respective time delays are imparted to a plurality of pulsers 24 by a transmit beamformer 26. Master controller 20 determines the conditions under which the acoustic pulses will be transmitted. With this information, transmit beamformer 26 determines the timing and amplitudes of each of the transmit pulses to be generated by pulsers 24. The amplitudes of each transmit pulse are generated by an apodization generation circuit 36, which may be a high-voltage controller that sets the power supply voltage to each pulser. Pulsers 24 in turn send the transmit pulses to each of elements 12 of transducer array 10 via T/R switches 18, which protect time-gain control (TGC) amplifiers 28 from the high voltages which may exist at the transducer array. Weightings are generated within apodization generation circuit 36, which may comprise a set of digital-to-analog converters that take the weighting data from transmit beamformer 26 and apply it to pulsers 24. By appropriately adjusting the transmit focus time delays in a conventional manner and also adjusting the transmit apodization weightings, an ultrasonic beam can be directed and focused to form a transmit beam. The apodization weightings and the transmit focus delays may be set by the master controller 20 based on system programming and operator inputs.

The echo signals produced by each burst of ultrasonic energy are backscattered from objects located at successive ranges along each transmit beam. The backscattered echo signals are sensed separately by each transducer element 12 and a sample of the magnitude of the echo signal at a particular point in time represents the amount of reflection occurring at a specific range. Due to differences in the propagation paths between a reflecting point and each transducer element 12, the echo signals from a specific range will not be detected simultaneously by each transducer element 12 and their amplitudes will not be equal. Receiver 16 amplifies the separate echo signals via a respective TGC amplifier 28 in each receive channel. The amount of amplification provided by the TGC amplifiers is controlled through a control path (not shown) that is driven by a TGC circuit (not shown), the latter being set by the master controller and hand operation of potentiometers. The amplified echo signals are then fed to a receive beamformer 30. Each receiver channel of the receive beamformer is coupled to a respective one of transducer elements 12 by a respective TGC amplifier 28.

Under the direction of master controller 20, receive beamformer 30 tracks the direction of the transmitted beam. Receive beamformer 30 imparts the proper time delays and receives apodization weightings to each amplified echo signal and sums them to provide an echo signal which accurately indicates the total ultrasonic energy reflected from a point located at a particular range along one ultrasonic beam. The receive focus time delays are computed in real-time using specialized hardware or are read from a look-up table. The receive channels also have circuitry for filtering the received pulses. The time-delayed receive signals are then summed and supplied to either a signal processor or detector 33 in one path for conventional B-mode processing, or to another signal processor or detector 32 for colorflow and/or Doppler flow processing. Master controller 20 selects between detectors 32 and 33 via a switch 35 to convert the summed receive signals to data suitable for display dependent on the type of transmit firing being transmitted. For B-mode (gray scale) data, detector 33 extracts the envelope of the returning signal, usually applying some additional processing, such as edge enhancement and logarithmic compression. For colorflow, detector 32 typically applies a high pass filter to remove stationary tissue signal, and extracts a phase shift which is an indication of the velocity of the moving blood. A scan converter 34 receives the display data from detectors 32, 33 and converts the data into the desired image for display. In particular, scan converter 34 converts the acoustic image data from polar coordinate (R-Θ) sector format or Cartesian coordinate linear array to appropriately scaled Cartesian coordinate display pixel data at the video rate. These scan-converted acoustic data are then provided for display on display monitor 22, which images the time—varying amplitude of the signal envelope as a gray scale. A respective scan line is displayed for each transmit beam.

In the conventional system, the special flow and/or contrast imaging modes, such as B-flow, CHA, and CA, are typically processed using the B-mode detector 33, and detector 32 is either unused or continues to be used for Doppler processing.

Figure 2:
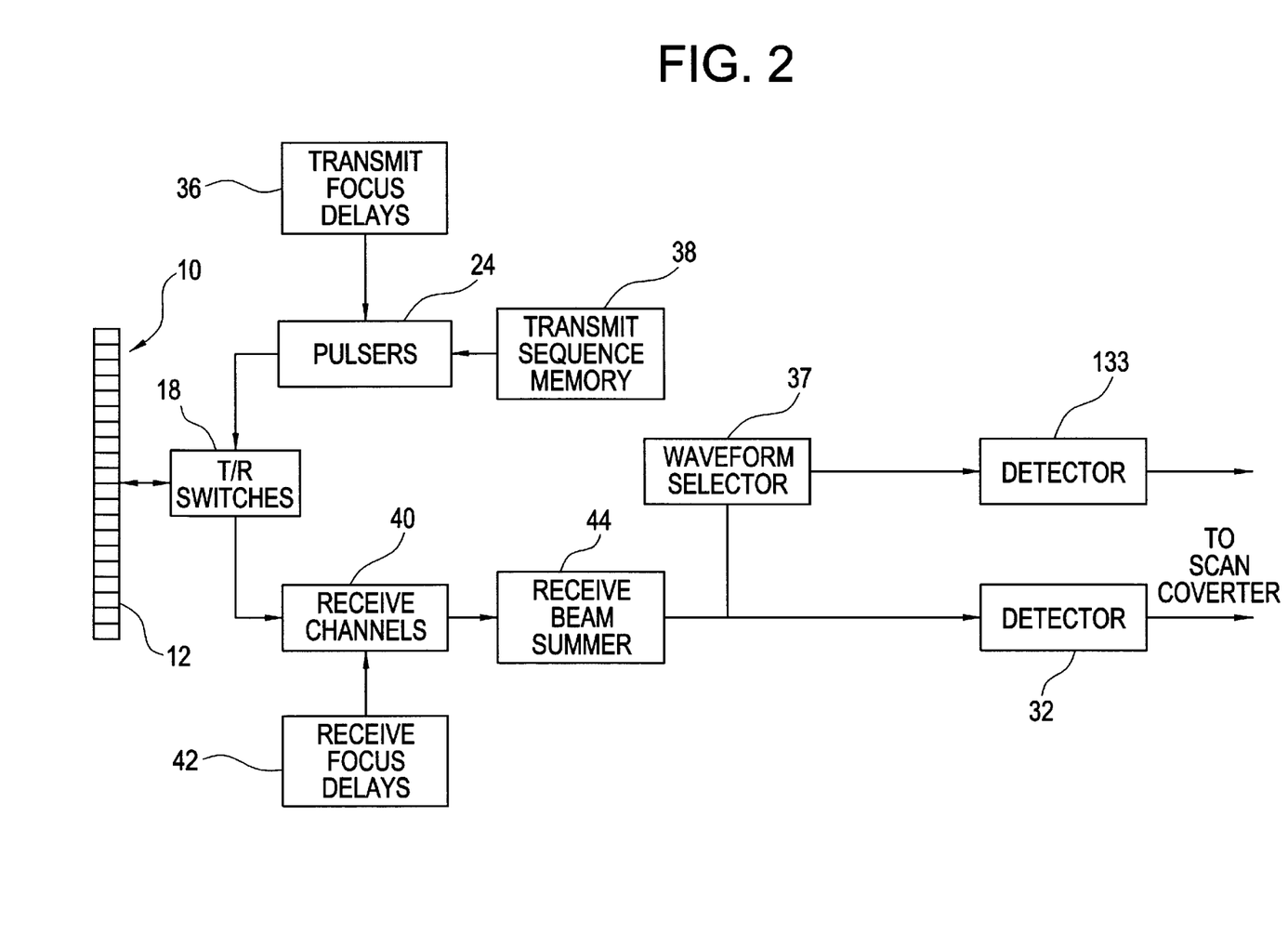
FIG. 2 is a block diagram of an ultrasound imaging system in accordance with an exemplary embodiment of the disclosure.

FIG. 2 shows an ultrasound flow imaging system in accordance with an exemplary embodiment for use in medical diagnostics. In this system, each transducer element 12 in the transmit aperture is pulsed N times (where N is preferably 2 to 4) using a possibly coded waveform. The appropriate waveform to be transmitted is supplied by the transmit sequence memory 38 to each pulser for each firing. Pulsers 24 drive elements 12 of transducer array 10 such that the ultrasonic energy produced is directed or steered in a beam for each transmit firing. To accomplish this, transmit focus time delays 36 are imparted to the respective pulsed waveforms produced by the pulsers in response to transmit sequence 38. By appropriately adjusting the transmit focus time delays in a conventional manner, the ultrasonic beam can be focused at a desired transmit focal position.

For each transmit, the return echo signals from transducer elements 12 are fed to respective receive channels 40 of the receive beamformer. Under the direction of master controller 20 (FIG. 1), the receive beamformer tracks the direction of the transmitted beam. The receive beamformer imparts the proper receive focus time delays 42 to the received echo signal and sums them to provide an echo signal which accurately indicates the total ultrasonic energy reflected from a particular position along a transmit beam. The time-delayed receive signals are summed in a receive summer 44 for each of the N transmit firings focused at a particular transmit focal position.

Figure 3:
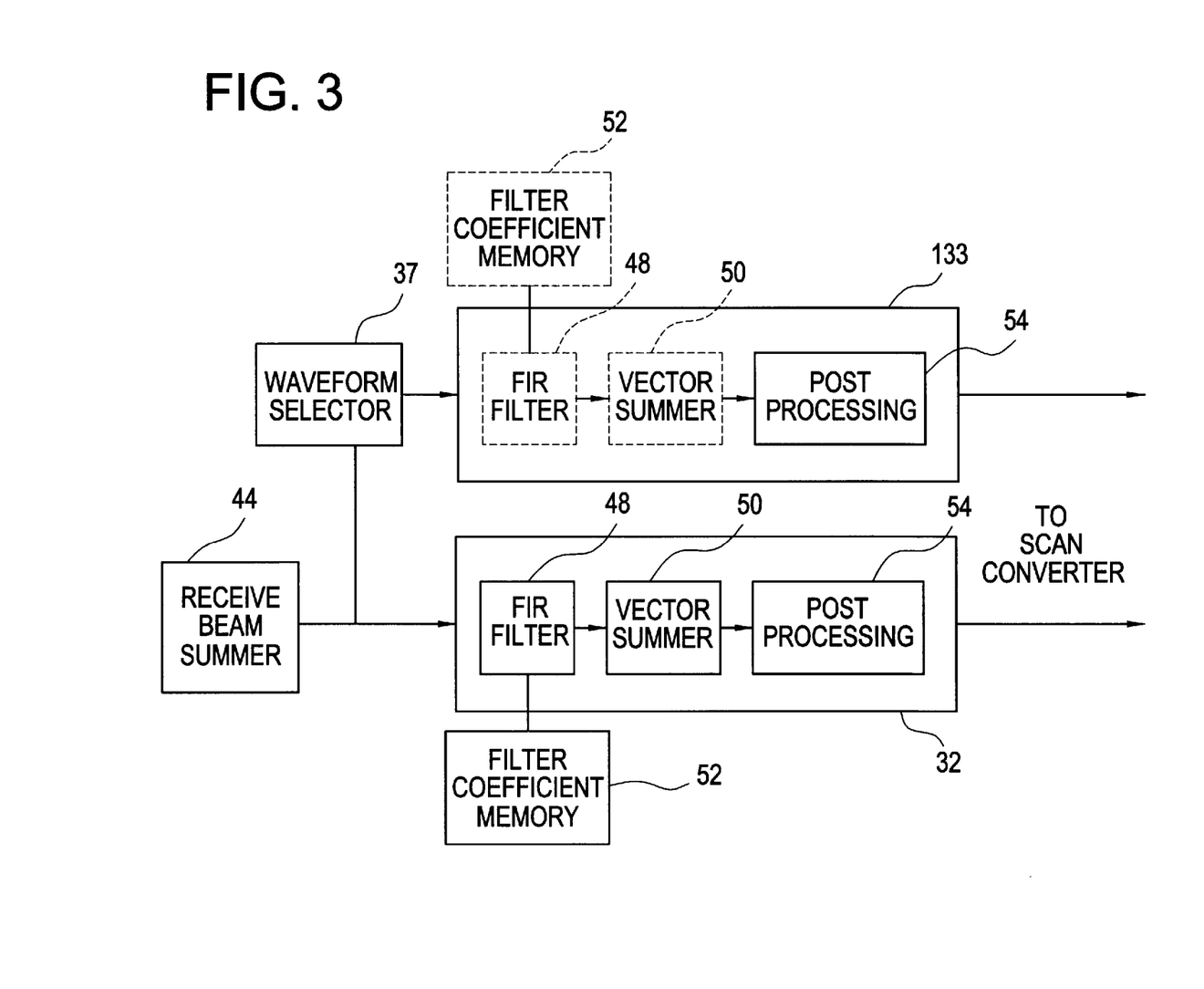
FIG. 3 is a block diagram showing two independent processors/detectors of FIG. 2 in more detail to formulate a reference image and a flow image.

Referring to FIGS. 2 and 3, the summed receive signals for successive transmit firings are received in detector 32 and are possibly decoded if a coded waveform has been transmitted, bandpass filtered, and provided to a wall filter, which filters across the N transmit firings and then supplies a filtered signal to a post processing unit 54. Post processing unit 54 forms the envelope of the firing-to-firing filtered signal, and performs optional compression and/or further post-processing.

Another signal processor or detector 133 selects at least one of the N transmit firings via a waveform selector 37, performs decoding if a coded waveform has been selected, and processes the same simultaneously with processing in detector 32 discussed above for providing a separate signal indicative of a stationary or slowly moving structure, e.g., background tissue. Waveform selector 37 is optionally controlled by master controller 20 by configuring master controller 20 to select at least one of the firings of the N transmit firings. After post-processing (including possible edge enhancement and logarithmic compression) and scan conversion of the two signals from detectors 32, 133, a scan line is displayed on display monitor 22 (FIG. 1). This procedure is repeated so that a respective scan line is displayed for each transmit focal position (in the case of one transmit focal position for each beam angle) or for each vector (in the case of multiple transmit focal positions for each beam angle).

In accordance with one exemplary embodiment of the invention still referring to FIGS. 2 and 3, detector 32, which processes the flow/contrast agent signal, includes a filter 46 further comprising an FIR filter 48 having an input coupled to the output of receive beam summer 44; and a vector summer 50 having an input coupled to FIR filter 48 and an output coupled to envelope detection and optional further post processing 54. The FIR filter effectively combines pulse compression, if coded excitation is being used, bandlimiting, and together with the vector summer, the wall filter. The FIR filter has M filter taps for receipt of a respective set of M filter coefficients for each transmit firing. The filter coefficients for the n-th transmit firing are $a_n c_0^n, a_n c_1^n, \ldots, a_n c_{M-1}^n$, where $a_n$ is the scalar weighting for the n-th transmit firing, $n=0, 1, \ldots, N-1$, and $c_0^n, c_1^n, \ldots, c_{M-1}^n$ is a set filter coefficients which are selected so that FIR filter 48 passes a major fraction of the desired fundamental frequencies or desired (sub/ultra) harmonic frequencies in the receive signal. If a coded waveform has been transmitted, the $c_0, c_1, \ldots c_{M-1}$ coefficients also include the pulse compression decoding filter. The scalar weightings $a_0, a_1, \ldots, a_{N-1}$ form a "wall" filter in slow time which selectively passes signals from reflectors moving at a velocity greater than a predetermined threshold. The filter coefficients $a_n c_0, a_n c_1, \ldots, a_n c_{M-1}$ are supplied to the filter for each transmit firing by the master controller from a filter coefficient memory 52. For example, for the first transmit firing, the set of filter coefficients $a_0c_0, a_0c_1, \ldots, a_0c_{M-1}$ is supplied to the FIR filter; for the second transmit firing, the set of filter coefficients $a_1c_0, a_1c_1, \ldots, a_1c_{M-1}$ is supplied to the FIR filter; and so forth. The filter coefficients are programmable depending upon the diagnostic application. Different sets of filter coefficients can be stored in look-up tables inside the master controller memory and the desired set of coefficients can be selectable by the system operator. For applications where the number of transmit firings N=2, pairs of sets of filter coefficients are stored in memory, one set of filter coefficients of a selected pair being transferred to the FIR filter before the first transmit firing and the other set of filter coefficients of the selected pair being transferred to the FIR filter after the first transmit firing and before the second transmit firing. Similarly, for applications where the number of transmit firings N=3, two or three sets of filter coefficients are stored in memory for use in filtering the receive signals resulting from the first through third firings. A similar procedure is enacted for applications where the number of transmit firings N>3. The successive FIR filter output signals for the N transmit firings are accumulated in a vector summer 50. The output signal of the vector summer then undergoes conventional B-mode processing (envelop detection and logarithmic compression), followed by scan conversion and display.

Still referring to FIGS. 2 and 3, detector 133 includes an input to receive at least one transmit firing from waveform selector 37 for generating a B-mode reference using detector 133 as a second B-mode processor for simultaneous and independent processing of a subset of the transmit firings used to form a flow/contrast agent image signal in detector 32. The input of detector 133 receives at least one transmit firing from the multiple firing group processed in detector 32, and passes it through FIR filter 48, which applies pulse compression if a coded waveform has been transmitted and performs bandwidth limiting. It has P filter taps for receipt of a respective set of P filter coefficients for each transmit firing. The filter coefficients $d_0, d_1, \ldots, d_{P-1}$, where $d_0, d_1, \ldots, d_{M-1}$ is a set of filter coefficients which are selected so that FIR filter 48 passes a major fraction of the desired fundamental frequencies or desired (sub/ultra) harmonic frequencies in the receive signal. If a coded waveform has been transmitted, the $d_0, d_1, \ldots d_{P-1}$ coefficients also include the pulse compression decoding filter. The filter coefficients $d_0, d_1, \ldots, d_{P-1}$ are supplied to the filter for each transmit firing by the master controller from a filter coefficient memory 52. The filter coefficients are again programmable depending upon the diagnostic application. Different sets of filter coefficients can be stored in look-up tables inside the master controller memory and the desired set of coefficients can be selectable by the system operator. In the case of transmitting uncoded wave forms, or coded waveforms that only require one firing for decoding, have been transmitted, only one firing is input to detector 133, and only one set of filter coefficients needs to be supplied by Filter Coefficient Memory 52. In the case that codes requiring multiple firings for decoding are used, such as Golay codes which require two firings to perform pulse compression, two waveforms are input to detector 133, and two sets of filter coefficients are used, one for each waveform. For applications where the number of transmit firings N=2, one set of filter coefficients of a selected pair is transferred to the FIR filter before the first transmit firing and the other set of filter coefficients of the selected pair being transferred to the FIR filter after the first transmit firing and before the second transmit firing. If the number of transmit firings input to detector 133 is more than 1 (as is the case for decoding Golay codes), successive FIR filter output signals for the multiple transmit firings are accumulated in a vector summer 50. The output signal of the vector summer then undergoes conventional B-mode processing (envelop detection and logarithmic compression), followed by scan conversion and display.

The time interval between each of the N transmits per focal position is user controllable to determine the "slow-time" filter cutoff frequency. A longer interval between each of the N transmits to a particular focal position results in a lower cutoff frequency with higher sensitivity to low velocity flow.

The flow/contrast agent image is optionally displayed by itself in one portion of display 22 for maximum image contrast, or may be overlayed with a B-mode background image. Superimposition of the flow image on a conventional B-mode image allows the diagnostician to observe the flow of blood relative to known anatomical landmarks during medical diagnosis.

Figure 4:
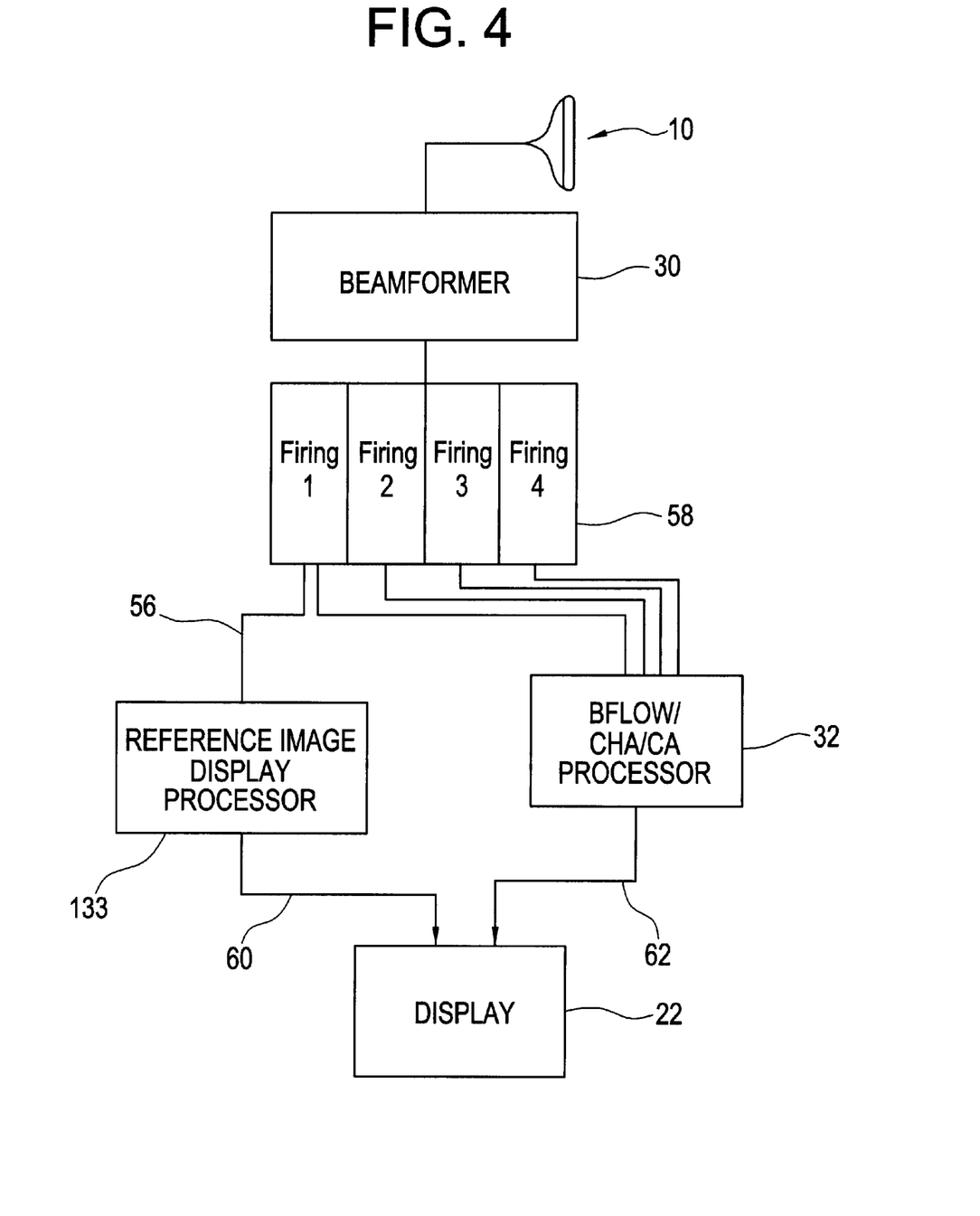
FIG. 4 is a block diagram showing independent processing of a one return signal from a multi-firing group used to generate a separate reference image signal to a display device in accordance with one preferred embodiment of the invention.

In one preferred embodiment depicted in FIG. 4, a traditional B-mode reference image is derived from one firing 56 of a multi-firing group 58 in B-flow, Coded Angio (CA), or Coded Harmonic Angio (CHA) imaging. More specifically, if single transmit firing codes are being used in B-flow, CHA and CA imaging, only one firing 56 from the multi-firing group 58 is required to form a traditional B-mode image. The single firing 56 is independently processed by processor/detector 133 separate from processing the multi-firing group 58 by processor/detector 32. Detector 133 generates a reference image signal 60 indicative of tissue background to display 22 while detector 32 generates a flow image signal 62 indicative of fluid flow or contrast agents to display 22. Reference image signal is further processed to provide a first image portion on display 22 indicative of stationary background for providing a reference image 100 (See FIGS. 6 and 7). Flow/contrast agent image signal 62 is further processed to provide a second image portion on display 22 indicative of fluid flow/contrast agent dynamics for providing a flow/contrast agent image 102 in conjunction with a corresponding flow image signal.

Figure 5:
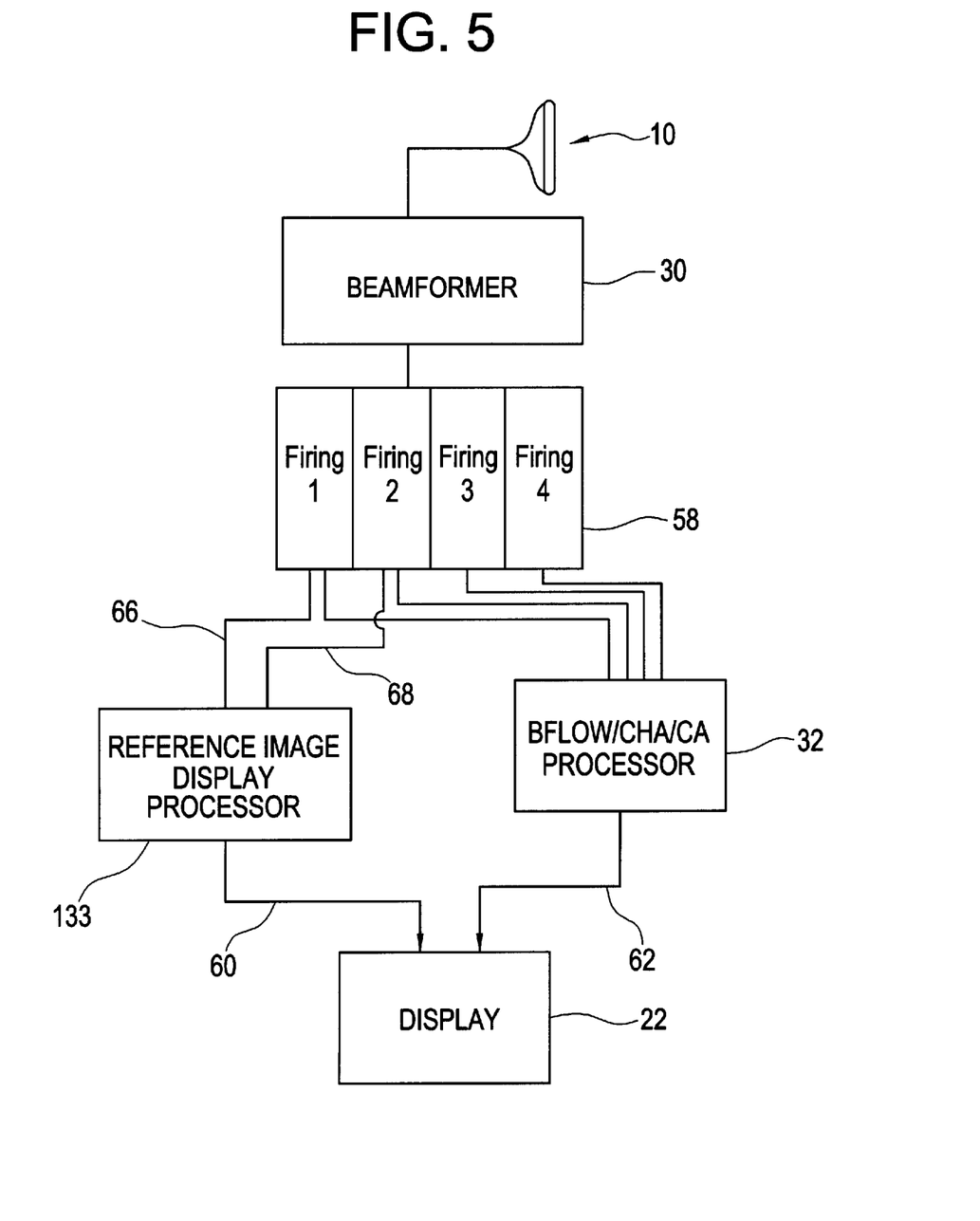
FIG. 5 is a block diagram showing independent processing of two return signals from a multi-firing group used to generate a separate reference image signal to a display device in accordance with one preferred embodiment of the invention.

In an alternate embodiment depicted in FIG. 5, two firings 66 and 68 (e.g., a pulse inverted pair) of the CHA multi-firing group 58, for example, are optionally used to form a harmonic reference image. Tissue imaging for the reference image can be improved by using harmonics (e.g., the $2^{nd}$, $3^{rd}$ or higher harmonics) which are at a frequency higher than the fundamental frequency. For example, harmonic imaging at twice the fundamental frequency can increase image quality due to higher spatial resolution, and also due to the presence of fewer artifacts or interference in the second harmonic signal than the signal at the fundamental frequency. This is due to the fact that harmonic frequencies are created along the wave propagation path rather than at the transmission source. As before, the two firings 66 and 68 are independently processed by processor/detector 133 separate from processing the multi-firing group 58 by processor/detector 32. Detector 133 generates reference image signal 60 indicative of tissue background to display 22 while detector 32 generates flow/contrast agent image signal 62 indicative of fluid flow/contrast agent to display 22. Reference image signal 60 is further processed to provide a first image portion on display 22 indicative of stationary background for providing a reference image 100 (See FIGS. 6 and 7). Flow/contrast agent image signal 62 is further processed to provide a second image portion on display 22 indicative of fluid flow/contrast agent dynamics for providing an image 102 in conjunction with a corresponding flow/contrast agent image signal.

In yet another example using coded excitation, as many firings as are necessary in the decoding process are received in processor 133. For example, if Golay codes are being used in the B-flow firing sequence, two firings from the number being transmitted are necessary to properly decode the codes. Coded transmission can further increase the signal amplitude and SNR by transmitting a waveform at the amplitude of the regular transmission method but of a longer pulse duration. The instantaneous power in the coded transmission is the same as in the regular transmission. However, the coded transmission method transmits more energy by transmitting a longer ultrasound waveform, therefore penetration is typically greater for coded waveforms than for waveforms that are uncoded.

A pair of Golay-encoded base sequences are formed by convolving a base sequence with a Golay code pair after oversampling. A Golay code pair is a pair of binary (+1, −1) sequences with the property that the sum of the autocorrelations of the two sequences is a Kronecker delta function. An oversampled Golay sequence is the Golay sequence with zeroes between each +1 and −1, the number of zeroes being greater than or equal to the length of the base sequence minus one. Golay codes have no range sidelobes when decoded. For each firing, decoding is performed using the oversampled Golay sequence corresponding to the Golay-encoded base sequence employed during transmission. By transmitting two sequences of pulses that are polarity-encoded according to a Golay pair, correlation of each of the received beamsum signals with its corresponding oversampled Golay sequence and the summation of those correlations enables an increase in the SNR with virtually no degradation in image resolution or contrast. In practice, range sidelobes do occur due to code distortion, but tend to be below the noise floor and do not adversely affect image quality. Tissue motion that occurs between transmission of the two sequences of the Golay pair also causes code distortion, which increases the range sidelobes. By transmitting the second sequence as soon as the echoes from the first sequence are completely received, the time interval between the two transmits can be minimized. Minimization of the interval between transmits minimizes the motion-induced code distortion.

In each of the embodiments illustrated in FIGS. 4 and 5, the waveforms forming the reference image 100 is generated using a subset of those already being transmitted for the B-flow, CHA, or CA processing, thus not affecting the frame rate. The subsequent processing of these waveforms to provide the reference image is completely independent of the B-flow, CHA, or CA processing. In such case, the reference image quality is independently optimized. For example the receive frequency band can be adjusted to allow the reference image to be filtered (single firing) harmonic image rather a simple fundamental B-mode image.

In addition, since the reference image 100 is formed from a subset of the multiple firings 58 already being fired, the reference image 100 is simultaneously displayed with the subtraction mode images. This is in contrast with colorflow, where the firings for the color image and underlying B-mode are done separately leaving some temporal discrepancy between the two images. The temporal discrepancy is particularly obvious when the scanning frame rates are low.

Figure 6:
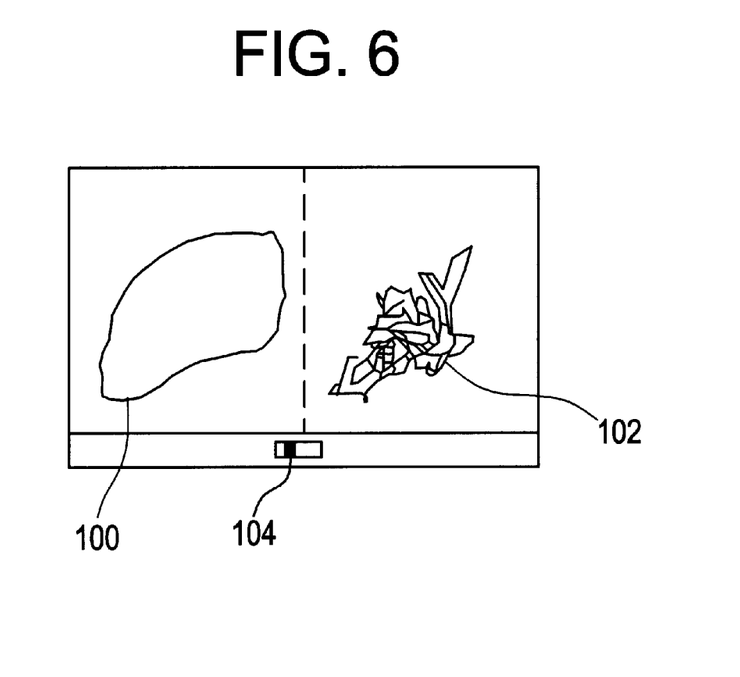
FIG. 6 is a schematic diagram of a display device showing one video format for viewing a reference image and a flow image.
Figure 7:
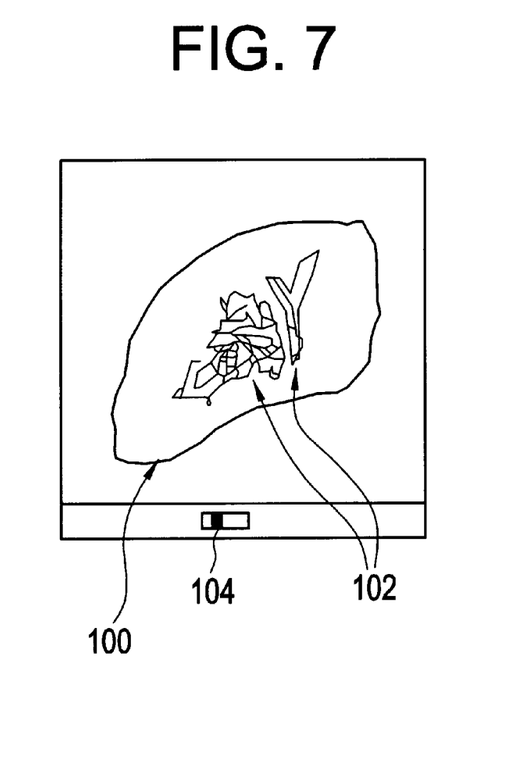
FIG. 7 is a schematic diagram of the display device of FIG. 5 showing an alternative video format for viewing a reference image and a flow image.

Referring to FIGS. 6 and 7, multiple display formats can be employed to display the subtraction mode flow image 102 and the reference image 100. In one embodiment depicted in FIG. 6, a side-by-side multi-image format is shown with the B-flow/CHA/CA flow image 102 displayed on one side of monitor 22, while the reference image 100 is simultaneously displayed on the other side. In an alternate embodiment illustrated in FIG. 7, the reference image is optionally used as an overlay image to the B-flow/CHA/CA flow image 102. The overlay is preferably such that it is transparent allowing the user to visualize the B-flow/CHA/CA flow image 102 underlying the reference image 100. Alternatively, one of the images is optionally colorized while keeping the other image in shades of gray. In yet another embodiment, the B-mode reference image 100 is optionally overlaid in areas where a B-flow/CHA/CA signal is absent, using a thresholding or adaptive process to determine whether to display the reference image 100 or B-flow/CHA/CA flow image 102. Finally, the B-mode reference image can be used as the underlying image, with the B-flow/CHA/CA used as the overlay, with the same image combination means (transparency, colorizing, thresholding) as described above. The above described display modes preferably include switch 104 to allow a sonographer the option to quickly toggle the reference image 100 on and off for optimizing the visualization of the dynamics of fluid flow under study.

When using a single-transmit code, exemplar embodiments require at least two transmits of the code, with the resulting echoes being "slow-time" filtered by the wall filter. In contrast, using Golay codes, acquisition of two data points at different times requires four transmits, two for each Golay code of the Golay code pair. Therefore, use of two-transmit codes requires at least four coded transmits. During wall filtering, the same set of scalar weightings are applied to the echoes of both Golay codes of the Golay code pair. Additional uncoded transmits can be included in the packet to acquire a harmonic B-mode background image, as previously described.

One way to significantly increase the flow contrast (i.e., visibility from background) is to use contrast agents in the fundamental mode. Contrast agents are typically encapsulated gas microbubbles between 0.1 and 10 microns in diameter. When introduced into the body through injection, contrast agents serve as high-reflectivity markers for blood flow and perfusion. Ultrasound energy incident on the microbubbles is strongly reflected at the incident (fundamental) frequencies and at resonant (harmonic and subharmonic) frequencies, such that both fundamental and harmonic imaging techniques are used to image contrast agent. The preferred method uses the harmonic frequencies and not the fundamental frequencies within the contrast echoes. Multiple firings of identical pulses are transmitted to a particular transmit focal position in succession. Specifically, N coded pulses centered at a fundamental frequency $f0$ are transmitted to each transmit focal position. On receive, an FIR filter centered at the fundamental frequency compresses the received pulses and substantially isolates the desired fundamental component. Subsequently a wall filter extracts the fundamental flow signal over the N transmits.

Although only certain preferred features of the invention have been illustrated and described, many modifications and changes will occur to those skilled in the art. For example, the invention is not limited to using biphase codes; polyphase codes can also be used. It is, therefore, to be understood that the appended claims are intended to cover all such modifications and changes as fall within the true spirit of the invention.

One of the advantages of the disclosure is that the above described embodiments address complaints from sonographers about the inability to visualize tissue background without degrading the fundamental quality of the desired B-flow/CHA/CA image. A second advantage of the disclosure is that the flow image may be displayed by itself for maximum flow contrast, or may be overlayed or side-by-side with a B-mode background image. Superimposition of the flow image on a conventional B-mode image allows the diagnostician to observe the blood flow relative to known anatomical landmarks during medical diagnosis.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method for displaying ultrasound images, comprising:
   transmitting at least first and second broadband pulses to a common transmit focal position;
   receiving at least first and second ultrasound reflections associated with said at least first and second broadband pulses;
   forming a flow/contrast agent signal component based on said at least first and second ultrasound reflections;
   forming a B-mode background signal component based on independent processing of at least one of said at least first and second ultrasound reflections; and
   displaying an ultrasound image including a flow image component in a first image portion of a display and a B-mode reference image component based on said at least one of said at least first and second ultrasound reflections, said B-mode reference image component displayed in a second image portion of said display.

2. The method of claim 1, wherein the transmitting step includes generating one of a coded and an uncoded waveform for multiple pulses.

3. The method of claim 2, further comprising: forming an envelope of a signal including said flow/contrast agent signal component and said B-mode background signal component.

4. The method of claim 1, further comprising: wall filtering across said first and second ultrasound reflections.

5. The method of claim 4, further comprising: passing fundamental frequency components of a signal including said flow/contrast agent signal component and said B-mode background signal component.

6. The method of claim 1, further comprising: passing harmonic frequency components of a signal including said flow/contrast agent signal component and said B-mode background signal component.

7. The method of claim 1, further comprising: passing subharmonic frequency components of a signal including said flow/contrast agent signal component and said B-mode signal component.

8. The method of claim 1, further comprising: passing ultraharmonic frequency components of a signal including said flow/contrast agent signal component and said B-mode signal component.

9. The method of claim 1, wherein the transmitting step includes transmitting a sequence of identical broadband pulses, centered at a fundamental frequency, to a particular transmit focal position.

10. The method of claim 1, further comprising: bandpass filtering a fundamental frequency of said first and second ultrasound reflections substantially isolating a desired component of ultrasound reflections.

11. The method of claim 1, wherein the transmitting step includes encoding said sequence of at least two pulses with transmit codes to form a packet of coded broadband pulses transmitted with a given pulse repetition interval to a transmit focal position, said packet including up to four pulses.

12. The method of claim 1, wherein the transmitting step includes modulating each of said pulses with a predefined code sequence, each of said pulses having a predetermined transmit burst length.

13. The method of claim 1, wherein the transmitting step includes modulating first and second pulses with first and second separate predefined code sequences, respectively.

14. The method of claim 1, wherein the transmitting step includes modulating first through fourth pulses with first through fourth Golay code pair sequences, respectively.

15. The method of claim 1, wherein said first image portion and second image portion are side-by-side on said display.

16. The method of claim 1, wherein said first image portion and second image portion are juxtaposed on said display configured to allow an overlay display format of said flow image component and said B-mode reference image component.

17. The method of claim 16, wherein said overlay display format is configured to display said B-mode reference image component when said flow image component is absent.

18. The method of claim 17, wherein said overlay display format is configured to determine whether to display said B-mode reference image component using one of a thresholding and an adaptive process.

19. The method of claim 1, wherein said display includes a switch for operably switching said second image portion on and off.

20. A method to visualize tissue background and low amplitude signals simultaneously, without restricting visualization of the low amplitude signals, the method comprising:
   creating a first image from a plurality of firings at a target to form corresponding waveforms;
   processing said waveforms to form said first image, wherein said first image is indicative of the low amplitude signal;
   displaying said first image on a display device;
   creating a second image from a subset of said plurality of firings to form a subset of said corresponding waveforms;
   processing said subset of said corresponding waveforms, wherein said second image is a B-mode image indicative of the tissue background proximate the flow signal; and
   displaying said second image on said display device.

21. The method of claim 20, wherein said display device is configured to independently alter visualization of said second image without affect to said first image.

22. A method of operating an imaging system comprising a multiplicity of transducer elements for transmitting wave energy in response to electrical activation and transducing returned wave energy into electrical signals, and a display monitor for displaying a image having a first image portion which is a function of a flow image signal and having a second image portion which is a function of a reference image signal, said method comprising:

(a) activating transducer elements of said array to transmit focused wave energy encoded with a transmit code during first and second transmit events;

(b) forming first and second receive signals from electrical signals produced by said transducer elements subsequent to said first and second transmit events respectively;

(c) forming a reference image signal derived at least in part from independent processing of at least one of said first and second receive signals;

(d) compressing, bandpassing and wall filtering first and second fundamental signal components of said first and second receive signals respectively to form a flow signal;

(e) forming a flow image signal derived at least in part from said flow signal; and (f) applying said flow image signal and said reference image signal to the display monitor, wherein said reference image is adjustable without affect to said flow image.

23. The method as recited in claim 22, further comprising:

(g) activating transducer elements of said array to transmit uncoded focused wave energy during a third transmit event;

(h) forming a third receive signal from electrical signals produced by said transducer elements subsequent to said third transmit event;

(i) bandpassing a harmonic signal component of said third receive signal; and (j) forming said reference image signal from independent processing of said harmonic signal component and said flow signal.

24. The method as recited in claim 22, further comprising:

(g) activating transducer elements of said array to transmit uncoded focused wave energy during third and fourth transmit events, said uncoded focused wave energy of said third transmit event being of opposite polarity to said uncoded focused wave energy of said fourth transmit event;

(h) forming third and fourth receive signals from electrical signals produced by said transducer elements subsequent to said third and fourth transmit events respectively;

(i) bandpassing respective harmonic signal components of said third and fourth receive signals while substantially canceling respective fundamental signal components of said third and fourth receive signals respectively to form a harmonic background signal; and (j) forming said reference image signal from independent processing of said harmonic background signal.

25. A method of operating an imaging system comprising a multiplicity of transducer elements for transmitting wave energy in response to electrical activation and transducing returned wave energy into electrical signals, and a display monitor for displaying an image having an image portion which is a function of a flow image signal, said method comprising of:

(a) activating transducer elements of said array to transmit focused wave energy encoded with a first Golay code of a Golay code pair during first and third transmit events and to transmit focused wave energy encoded with a second Golay code of said Golay code pair during second and fourth transmit events;

(b) forming first through fourth receive signals from electrical signals produced by said transducer elements subsequent to said first through fourth transmit events respectively;

(c) forming a reference image signal derived at least in part from independent processing of two of first through fourth receive signals;

(d) decoding, bandpassing and wall filtering first through fourth fundamental signal components of said first through fourth receive signals respectively to form a flow signal;

(e) forming a flow image signal derived at least in part from said flow signal; and (f) applying said flow image signal and said reference image signal to the display monitor, wherein said reference image is adjustable without affect to said flow image.

26. An ultrasound medical diagnostic system for imaging stationary and moving reflectors for an area of interest in a patient, comprising:

a transmitter for transmitting a sequence of at least two pulses to a transmit focal position;

a receiver for receiving at least two echo signals associated with said sequence of at least two pulses, said echo signals containing a fundamental frequency component;

a first display processor configured to receive and process said at least two echo signals and having a filter for supplying a filtered signal containing flow image information for moving reflectors based on said at least two echo signals, a second display processor configured to receive and independently process at least one of said at least two echo signals containing B-mode information for stationary reflectors based on said at least two echo signals, said B-mode information for stationary reflectors including said fundamental frequency component; and a display for displaying a flow image of moving reflectors based on said filtered signal and a B-mode reference image of stationary reflectors based on said at least one of said at least two echo signals supplied by said second display processor.

27. The system of claim 26, wherein said display is adapted to combine said flow image and said B-mode reference image in order to illustrate the flow of moving reflectors relative to stationary reflectors.

28. The system of claim 26, wherein said display is adapted to combine a colorized said flow image and a gray scale said B-mode image for display.

29. The system of claim 26 further comprising means for amplitude detection of said filtered output signal to form a flow image signal.

30. The system of claim 26, wherein said transmitter is adapted to encode said sequence of at least two pulses with transmit codes to form a packet of coded broadband pulses transmitted with a given pulse repetition interval to a transmit focal position, said packet including up to four pulses.

31. The system of claim 26, wherein the transmitter is adapted to modulate each of said pulses with a predefined code sequence, each of said pulses having a predetermined transmit burst length.

32. The system of claim 26, wherein the transmitter is adapted to modulate first and second pulses with first and second separate predefined code sequences, respectively.

33. The system of claim 26, wherein the transmitter is adapted to modulate first through fourth pulses with first through fourth Golay code pair sequences.

34. An imaging system comprising:

a transducer array having a multiplicity of transducer elements for transmitting wave energy centered at a fundamental frequency in response to electrical activation and for transducing returned wave energy into electrical signals;

a display monitor for displaying an image having a first image portion which is a function of a flow image signal and a second image portion which is a function of a B-mode reference image signal; and a computer programmed to perform:
(a) activating transducer elements of said array to transmit focused wave energy encoded with a transmit code during first and second transmit events;
(b) forming first and second receive signals from electrical signals produced by said transducer elements subsequent to said first and second transmit events respectively;
(c) processing at least one of said first and second receive signals to form a B-mode signal;
(d) compressing, bandpassing and wall filtering first and second fundamental signal components of said first and second receive signals respectively to form a flow signal;
(e) forming a B-mode reference image signal derived at least in part from said B-mode signal;
(f) forming a flow image signal derived at least in part from said flow signal; and
(g) applying said B-mode image signal and said flow image signal to said display monitor.

35. The system as recited in claim 34, wherein said first image portion and second image portion are side-by-side on said display.

36. The system of claim 34, wherein said first image portion and second image portion are juxtaposed on said display configured to allow an overlay display format of said flow image signal and said B-mode reference image signal.

37. The system of claim 36, wherein said overlay display format is configured to display said B-mode reference image signal when said flow image signal is absent.

38. The system of claim 37, wherein said overlay display format is configured to determine whether to display said B-mode reference image signal using one of a thresholding and an adaptive process.

39. The system of claim 34, wherein said display includes a switch for operably switching said second image portion on and off.

40. The system as recited in claim 34, wherein said transducer elements comprise piezoelectric elements for transmitting ultrasound waves in response to electrical activation and for transducing returned ultrasound waves into electrical signals.

* * * * *